United States Patent [19]

Dusza et al.

[11] 4,393,217

[45] Jul. 12, 1983

[54] SUBSTITUTED PHENYL-5-AMINOPYRAZOLES

[75] Inventors: John P. Dusza; Jay D. Albright, both of Nanuet, N.Y.

[73] Assignee: American Cyanamid Company, Stamford, Conn.

[21] Appl. No.: 224,606

[22] Filed: Jan. 12, 1981

[51] Int. Cl.$^3$ ............................................ C07D 231/38
[52] U.S. Cl. .................................. 548/362; 424/273 P
[58] Field of Search ........................................... 548/362

[56] References Cited

U.S. PATENT DOCUMENTS 3,939,161  2/1976  Ratajczyk et al. ................ 544/118
4,134,987  1/1979  Huppatz ........................... 424/273 P
4,346,097  8/1982  Schweiss et al. ................ 424/273 P

OTHER PUBLICATIONS

Wiley, Ed., Pyrazoles, Pyrazolines, Pyrazolidines, Indazoles and Condensed Rings, Interscience, New York, 1967, p. 89.

*Primary Examiner*—Henry R. Jiles
*Assistant Examiner*—Natalia Harkaway
*Attorney, Agent, or Firm*—Edward A. Conroy, Jr.; Anne M. Rosenblum

[57] ABSTRACT

This disclosure describes novel substituted phenyl-5-aminopyrazoles useful as anxiolytic and/or anti-depressant agents.

3 Claims, No Drawings

SUBSTITUTED PHENYL-5-AMINOPYRAZOLES

BRIEF SUMMARY OF THE INVENTION

This invention relates to new organic compounds and more particularly is concerned with novel substituted phenyl-5-aminopyrazoles which have anxiolytic and/or anti-depressant activity. The compounds of the present invention may be represented by the following structural formula:

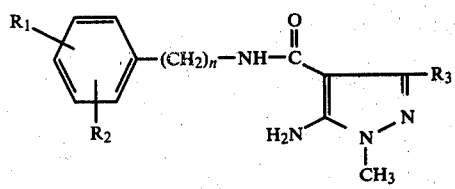

wherein $R_1$ and $R_2$ may be the same or different and may be selected from the group comprising hydrogen, bromo, chloro, fluoro, lower alkyl ($C_1$–$C_3$) and pyrrolyl; $R_3$ is selected from the group comprising hydrogen and lower alkyl ($C_1$–$C_3$), and n is 0 or 1.

This invention is also concerned with the compound 5-amino-N,1-dimethyl-4-pyrazolecarboxy-o-toluidide which possesses anxiolytic activity and is represented by the following structure:

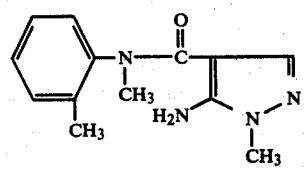

DETAILED DESCRIPTION OF THE INVENTION

The novel compounds of the present invention are in general pale yellow or colorless crystalline solids with characteristic melting points which are generally soluble in organic solvents such as lower alkanols, acetone, ethyl acetate, chloroform and dichloromethane.

Preparation of the novel substituted phenyl-5-aminopyrazoles (D) of this invention which exhibit anxiolytic and/or anti-depressant activity is instituted (Scheme I) by heating a cyanoacetanilide of formula (A) [prepared by the procedures described in U.S. Pat. No. 3,116,312] with N,N-dimethylformamide dimethylacetal for 2–6 hours. The volatiles are removed in vacuo. The resulting solid is dissolved in dichloromethane and the solution is passed through an absorbent pad of hydrous magnesium silicate. The effluent is crystallized by the addition of n-hexane. The mixture is cooled and filtered to provide the intermediate acrylanilide, acrylamide, acrylotoluidide, crotonanilide and acryloxylidide compounds (C).

SCHEME I

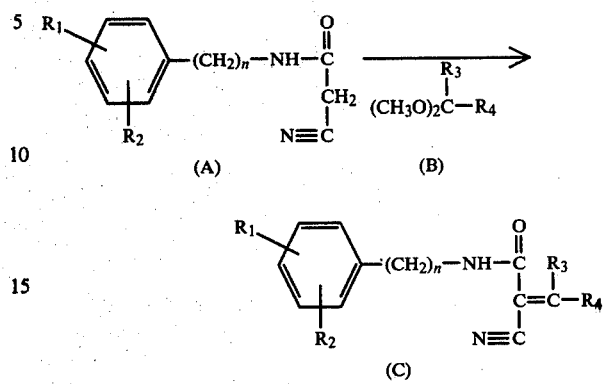

Wherein $R_1$, $R_2$ and n are as hereinabove defined and where $R_4$ is $(CH_3)_2N$ and $R_3$ is hydrogen. The intermediate compounds (C) where $R_4$ is $(CH_3)_2N$ and $R_3$ is $CH_3$ may also be prepared by the hereinabove described procedure by substituting N,N-dimethylacetamide dimethylacetal for N,N-dimethylformamide dimethylacetal (B) in Scheme I.

In addition, when the appropriate cyanoacetanilide (A) [prepared by the procedures described in U.S. Pat. No. 3,116,312] is refluxed with triethyl orthopropionate (B) (Scheme II) for 6 hours, and the volatiles are removed in vacuo a solid is obtained. The solid is recrystallized from ethanol to give the intermediate compounds (C) where $R_1$, $R_2$ and n are as previously defined and where $R_4$ is $OC_2H_5$ and $R_3$ is $C_2H_5$.

SCHEME II

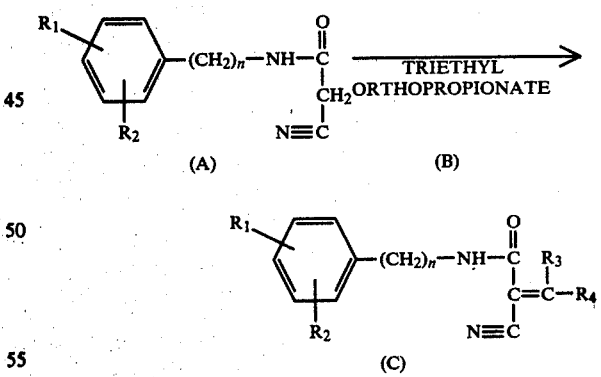

When the intermediate acrylanilide, acrylamide, acrylotoluidide, crotonanilide or acryloxylidide compound (C) (Scheme III) is dissolved in ethanol, then is refluxed for 15 hours in the presence of hydrazine hydrate (D), and the reaction mixture is evaporated in vacuo, a solid is obtained. The solid is washed in water and is collected by filtration. The crude product is recrystallized from acetone-n-hexane, dichloromethane-n-hexane or ethanol to give the desired product (E) where $R_1$, $R_2$, $R_3$ and n are previously defined.

SCHEME III

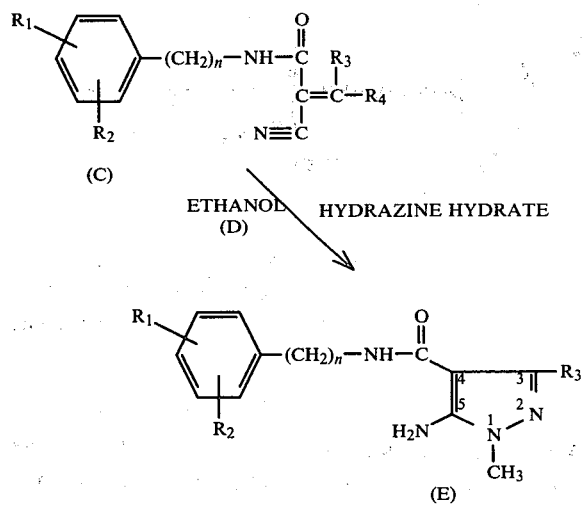

Some of the novel compounds of the present invention possess central nervous system activity at non-toxic doses and as such are useful as anxiolytic agents. That is, they produce certain responses in standard tests with laboratory animals which are known to correlate well with relief of anxiety in man.

The anti-anxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle, containing 5% v/v polyethylene glycol and one to two drops of polysorbate 80 to groups of at least 4 rats. At 30 or 60 minutes, the rats were treated intravenously with pentylenetetrazole at a dose of 23 mg./kg. of body weight. This dose is estimated to cause clonic seizures in 99% of unprotected rats. The test compounds are considered active if they protect 50% or more of the rats from clonic seizures. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pp. 237–288 (1971)] that there is a high degree of correlation between antagonism of pentylenetetrazole seizures in rats and anti-anxiety effects in higher warm-blooded animals. The following representative compounds of the present invention have been shown to possess anxiolytic activity when tested as described above.

5-Amino-3'-chloro-3-ethyl-1-methyl-4-pyrazolecarboxy-o-toluidide
5-Amino-4'-chloro-3-ethyl-1-methyl-4-pyrazolecarboxanilide
5-Amino-1-methyl-4-pyrazolecarboxy-2'-toluidide
5-Amino-2',5'-dichloro-1-methyl-4-pyrazolecarboxanilide
5-Amino-2'-isopropyl-1,3-dimethyl-4-pyrazolecarboxanilide
5-Amino-3'-ethyl-1-methyl-4-pyrazolecarboxanilide
5-Amino-6'-chloro-1-methyl-4-pyrazolecarboxy-o-toluidide
5-Amino-2'-ethyl-1,3-dimethyl-4-pyrazolecarboxanilide
5-Amino-2'-ethyl-1-methyl-4-pyrazolecarboxanilide
5-Amino-2'-chloro-1-methyl-4-pyrazolecarboxanilide
5-Amino-2'-bromo-1-methyl-4-pyrazolecarboxanilide
5-Amino-6'-chloro-α,α,α-trifluoro-1-methyl-4-pyrazolecarboxy-m-toluidide
5-Amino-N-1-dimethyl-4-pyrazolecarboxy-o-toluidide
5-Amino-1-methyl-4-pyrazolecarboxy-2',5'-xylidide
5-Amino-N-benzyl-1-methyl-4-pyrazolecarboxamide
5-Amino-N-o-chlorobenzyl-1-methyl-4-pyrazolecarboxamide
5-Amino-2'-fluoro-1-methyl-4-pyrazolecarboxanilide
5-Amino-2',6'-difluoro-1-methyl-4-pyrazolecarboxanilide
5-Amino-1-methyl-2'-(1-pyrrolyl)-4-pyrazolecarboxanilide Some of the final products possess anti-depressant activity as established by the inhibition of tetrabenazine induced depression of exploratory behavior in mice. In this test, doses of 25 mg./kg. or less of body weight of the test compounds are administered intraperitoneally or orally to groups of 5 mice one hour before the administration of tetrabenazine hexamate at an intraperitoneal dose of 30 mg./kg. of body weight which is known to depress markedly the exploratory behavior of normal mice. Thirty minutes later the mice are tested for their exploratory behavior. Individual mice are placed in the center of a horizontal disc (approximately 18 inches in diameter). Inhibition of the depression induced by tetrabenazine is considered present if the mice perform one or more of the following actions within 10 seconds after being placed on the disc:

(1) Animals move to the edge of the disc and look over the edge
(2) Animals move 180° in place
(3) Animals display a head movement of 90° immediately followed by a head movement in the opposite direction of at least 45°.

Administration of the test compounds to additional groups of 5 mice is repeated, the numbers of individual animals showing an anti-depressant response (normal exploratory behavior) is recorded and the results are analyzed by the following scheme:

| | No. Active/No. Tested | |
|---|---|---|
| 1st Stage (5 animals) | 0/5 | Reject (ineffective anti-depressant) |
| | 1/5–3/5 | Continue to Stage 2 |
| | ≧4/5 | Accept (active anti-depressant) |
| 2nd Stage | 1/5 | Reject |
| | 2/10–3/10 | Continue to Stage 3 |
| | ≧4/10 | Accept |
| 3rd Stage | <4/15 | Reject |
| | ≧4/15 | Accept |

This method has been described by Greenblatt, E. N. and Osterberg, A. C. in Toxicology and Applied Pharmacology 7, 566–578 (1965). The following representative compounds of the present invention have been shown to possess anti-depressant activity when tested as described above.

5-Amino-1-methyl-4-pyrazolecarboxanilide
5-Amino-2',5'-dichloro-1-methyl-4-pyrazolecarboxanilide
5-Amino-2'-ethyl-1-methyl-4-pyrazolecarboxanilide
5-Amino-2'-chloro-4'-fluoro-1-methyl-4-pyrazolecarboxanilide
5-Amino-2',5'-difluoro-1-methyl-4-pyrazolecarboxanilide Some of the novel compounds of the present invention have been found to be highly useful for meliorating anxiety in mammals when administered in amounts ranging from about 0.5 mg. to about 50.0 mg./kg. of body weight per day. A preferred dosage regimen for optimum results would be from about 1.0 mg. to about 20.0 mg./kg. of body weight per day. Such dosage units are employed that contain a total of from about 10 to about 200 mg. of active compound. This dosage regimen may be adjusted to provide the optimum therapeutic response. For example, several divided doses may be administered daily or the dose may be proportionally reduced as indicated by the exigencies of the therapeutic situation.

Some of the novel compounds of the present invention have also been found to be useful as an anti-depressant agents when administered in amounts ranging from about one mg. to about 30 mg./kg. of body weight per day. A preferred dosage regimen for optimum results would be from about 2.0 mg./kg. to about 15 mg./kg. of body weight per day, and such dosage units are employed that a total of from about 140 mg. to about 1000 mg. of active compound for a subject of about 70 kg. of body weight are administered in a 24 hour period. This dosage regimen may also be adjusted to provide the optimum therapeutic response as exemplified above.

The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl- and propylparabens, and thimerosal. As a practical matter, it is also convenient to employ antioxidants. Suitable antioxidants include, for example, sodium bisulfite, sodium metabisulfite and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of the active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl- and propylparabens as preservatives, a dye and flavoring such as cherry or orange flavor. Of course, any material used in preparing any dosage unit form should be pharmaceutically pure and substantially non-toxic in the amounts employed.

SPECIFIC DISCLOSURE

The following specific examples illustrate the preparation of the compounds of the present invention.

EXAMPLE 1

5-Amino-1-methyl-4-pyrazolecarboxanilide

A 10.0 g. amount of 2-cyanoacetanilide in 25 ml. of N,N-dimethylformamide dimethylacetal is heated on a steam bath for 2-6 hours. The reaction mixture volatiles are removed in vacuo and the resultant solid is dissolved in dichloromethane. The solution is passed through a short column of hydrous magnesium silicate, then n-hexane is added to the effluent until crystallization is noted. After cooling, the product is collected by filtration to give 2-cyano-3-dimethylamino-acrylanilide as colorless plates, m.p. 162.5°–164° C.

A 0.010 mole amount of the preceding compound is dissolved in 50 ml. of ethanol and 550 mg. of hydrazine hydrate is added. The reaction mixture is refluxed for 15 hours then is evaporated to dryness in vacuo. Water is added to the residue and the mixture is filtered to collect the crude product. The product is recrystallized from acetone-hexane to give the product of the Example as colorless prisms, m.p. 213.5°–215° C.

EXAMPLE 2

5-Amino-N-benzyl-1-methyl-4-pyrazolecarboxamide

As for Example 1, N-benzyl-2-cyanoacetamide, m.p. 122°–123° C., is heated with N,N-dimethylformamide dimethylacetal to give N-benzyl-2-cyano-3-dimethylaminoacrylamide as colorless needles, m.p. 160.5°–161° C.

A 0.010 mole amount of the above compound is refluxed in ethanol in the presence of hydrazine hydrate by the procedure of Example 1 to yield the product of the Example as colorless needles, m.p. 196.5°–198.5° C.

EXAMPLE 3

5-Amino-N-o-chlorobenzyl-1-methyl-4-pyrazolecarboxamide

As for Example 1, N-o-chlorobenzyl-2-cyanoacetamide, colorless needles, m.p. 108°–109° C., (prepared as described in U.S. Pat. No. 3,116,312) is heated with N,N-dimethylformamide dimethylacetal to give N-o-chlorobenzyl-2-cyano-3-dimethylaminoacrylamide as colorless needles, m.p. 144°–146.5° C.

A 0.010 mole amount of the preceding compound is refluxed in ethanol in the presence of hydrazine hydrate by the procedure of Example 1 to give the product of the Example as colorless needles, m.p. 200°–202.5° C.

EXAMPLE 4

5-Amino-2'-bromo-1-methyl-4-pyrazolecarboxanilide

As for Example 1, 2'-bromo-2-cyanoacetanilide, white crystals, m.p. 140°–141° C. (prepared as described in U.S. Pat. No. 3,116,312), is heated with N,N-dimethylformamide dimethylacetal to give 2'-bromo-2-cyano-3-dimethylaminoacrylanilide as off-white prisms, m.p. 91°–93° C.

A 0.010 mole amount of the preceding compound is refluxed in ethanol in the presence of hydrazine hydrate by the procedure of Example 1 to give the product of the Example as colorless plates, m.p. 194°–195° C.

EXAMPLE 5

5-Amino-2'-chloro-1-methyl-4-pyrazolecarboxanilide

As for Example 1, 2'-chloro-2-cyanoacetanilide, white crystalline product, m.p. 122.5°–123° C. (prepared as described in U.S. Pat. No. 3,116,312), is heated with N,N-dimethylformamide dimethylacetal to give 2'-chloro-2-cyano-3-dimethylaminoacrylanilide as colorless prisms, m.p. 104°–105° C.

A 0.010 mole amount of the above product is refluxed in ethanol in the presence of hydrazine hydrate by the procedure of Example 1 to give the product of the Example as colorless plates, m.p. 193°–194° C.

EXAMPLE 6

5-Amino-1-methyl-4-pyrazolecarboxy-2'-toluidide

As for Example 1, 2-cyano-o-acetotoluidide, a white crystalline product, m.p. 130°–133° C. (prepared as described in U.S. Pat. No. 3,116,312), is heated with N,N-dimethylformamide dimethylacetal to give 2-cyano-3-dimethylamino-o-acrylotoluidide as crystals, m.p. 86°–87° C.

A 0.010 mole amount of the preceding compound is refluxed in ethanol in the presence of hydrazine hydrate by the procedure of Example 1 to give the desired product 5-amino-1-methyl-4-pyrazolecarboxy-2'-toluidide as colorless plates, m.p. 194.5°–196° C.

EXAMPLE 7

5-Amino-2'-ethyl-1-methyl-4-pyrazolecarboxanilide

As for Example 1, 2-cyano-2'-ethylacetanilide as long needles, m.p. 128°–130° C. (prepared by the procedure described in U.S. Pat. No. 3,116,312), is heated with N,N-dimethylformamide dimethylacetal to yield 2-cyano-3-dimethylamino-2'-ethylacrylanilide as colorless prisms, m.p. 102.5°–104° C.

A 0.010 mole amount of the preceding product is refluxed in ethanol in the presence of hydrazine hydrate by the procedure of Example 1 to give the product of the Example as colorless plates, m.p. 220°–221° C.

EXAMPLE 8

5-Amino-3'-ethyl-1-methyl-4-pyrazolecarboxanilide

As for Example 1, 2-cyano-3'-ethylacetanilide as colorless plates, m.p. 98°–100° C. (prepared by the procedure described in U.S. Pat. No. 3,116,312), is heated with N,N-dimethylformamide dimethylacetal to give 2-cyano-3-dimethylamino-3'-ethylcrotonanilide as colorless prisms, m.p. 104°–106° C.

A 0.010 mole amount of the above compound is refluxed in ethanol in the presence of hydrazine hydrate by the procedure of Example 1 to give the desired product as colorless plates, m.p. 168°–170° C.

EXAMPLE 9

5-Amino-2',6'-difluoro-1-methyl-4-pyrazolecarboxanilide

As for Example 1, 2-cyano-2',6'-difluoroacetanilide as colorless crystals, m.p. 180°–181° C. (prepared by the procedure described in U.S. Pat. No. 3,116,312), is heated with N,N-dimethylformamide dimethylacetal to yield 2-cyano-3-dimethylamino-2',6'-difluoroacrylanilide as colorless crystals, m.p. 158°–159.5° C.

A 0.010 mole amount of the preceding product is refluxed in ethanol with hydrazine hydrate by the procedure of Example 1 to give the product of the Example as colorless crystals, m.p. 201°–203° C.

EXAMPLE 10

5-Amino-2',5'-difluoro-1-methyl-4-pyrazolecarboxanilide

As for Example 1, 2-cyano-2',5'-difluoroacetanilide, colorless crystals, m.p. 165°–167° C. (prepared by the procedure described in U.S. Pat. No. 3,116,312), is heated with N,N-dimethylformamide dimethylacetal to give 2-cyano-3-dimethylamino-2',5'-difluoroacrylanilide as colorless needles, m.p. 175°–176° C.

A 0.010 mole amount of the above product is refluxed in ethanol with hydrazine hydrate by the procedure of Example 1 to give the product of the Example as colorless platelets, m.p. 178°–180° C.

EXAMPLE 11

5-Amino-2',5'-dichloro-1-methyl-4-pyrazolecarboxanilide

As for Example 1, 2',5'-dichloro-2-cyanoacetanilide, as a white crystalline product, m.p. 190.5°–191.5° C. (prepared by the procedure described in U.S. Pat. No. 3,116,312), is heated with N,N-dimethylformamide dimethylacetal to yield 2-cyano-2',5'-dichloro-3-dimethylaminoacrylanilide as colorless needles, m.p. 175°–176° C.

A 0.010 mole amount of the preceding product is refluxed in ethanol in the presence of hydrazine hydrate by the procedure of Example 1 to give the desired product as colorless needles, m.p. 190°–191° C.

EXAMPLE 12

5-Amino-2'-chloro-4'-fluoro-1-methyl-4-pyrazolecarboxanilide

As for Example 1, 2'-chloro-2-cyano-4'-fluoroacetanilide as colorless needles, m.p. 138°–139° C. (prepared by the procedure described in U.S. Pat. No. 3,116,312), is heated with N,N-dimethylformamide dimethylacetal to give 2'-chloro-2-cyano-3-dimethylamino-4'-fluoroacrylanilide as colorless needles, m.p. 155.5°–156.5° C.

A 0.010 mole amount of the preceding compound is refluxed in ethanol with hydrazine hydrate by the procedure of Example 1 to yield the desired product as colorless needles, m.p. 176°–177° C.

EXAMPLE 13

5-Amino-6'-chloro-α,α,α-trifluoro-1-methyl-4-pyrazolecarboxy-m-toluidide

As for Example 1, 6'-chloro-2-cyano-α,α,α-trifluoro-m-acetotoluidide, white crystals, m.p. 152°–153° C. (prepared by the procedure described in U.S. Pat. No. 3,116,312), is heated with N,N-dimethylformamide dimethylacetal to give 6'-chloro-2-cyano-3-dimethylamino-α,α,α-trifluoro-m-acrylotoluidide as colorless needles, m.p. 158.5°–160° C.

A 0.010 mole amount of the above compound is refluxed in ethanol with hydrazine hydrate by the procedure of Example 1 to yield the product of the Example as colorless needles, m.p. 185°–186° C.

EXAMPLE 14

5-Amino-6'-chloro-1-methyl-4-pyrazolecarboxy-o-toluidide

As for Example 1, 6'-chloro-2-cyano-o-acetotoluidide as white crystals, m.p. 193°–194° C. (prepared by the procedure described in U.S. Pat. No. 3,116,312), is heated with N,N-dimethylformamide dimethylacetal to give 6'-chloro-2-cyano-3-dimethylamino-o-crotonotoluidide as colorless needles, m.p. 143°–145° C.

A 0.010 mole amount of the above compound is refluxed in ethanol in the presence of hydrazine hydrate by the procedure of Example 1 to give the product of the Example as colorless crystals, m.p. 229°–230° C.

EXAMPLE 15

5-Amino-1-methyl-4-pyrazolecarboxy-2',5'-xylidide

As for Example 1, 2-cyano-2',5'-acetoxylidide, a white crystalline material, m.p. 169°–170° C. (prepared by the procedure described in U.S. Pat. No. 3,116,312), is heated with N,N-dimethylformamide dimethylacetal to yield-2-cyano-17-dimethylamino-2',5'-acryloxylidide as colorless prisms, m.p. 153°–154.5° C.

A 0.010 mole amount of the preceding compound is refluxed in ethanol with hydrazine hydrate by the procedure of Example 1 to give the desired product as colorless plates, m.p. 222°–223° C.

EXAMPLE 16

5-Amino-1-methyl-2'-(1-pyrrolyl)-4-pyrazolecarboxanilide

As for Example 1, 2-cyano-2'-(1-pyrrolyl)acetanilide, colorless needles, m.p. 143°–144° C. (prepared by the procedure described in U.S. Pat. No. 3,116,312), is heated with N,N-dimethylformamide dimethylacetal to give 2-cyano-3-dimethylamino-2'-(1-pyrrolyl)acrylanilide as yellow crystals, m.p. 169°–171° C.

A 0.010 mole amount of the above compound is refluxed in ethanol with hydrazine hydrate by the procedure of Example 1 to yield the product of the Example as pale yellow crystals, m.p. 167°–169° C.

EXAMPLE 17

5-Amino-N,1-dimethyl-4-pyrazolecarboxy-o-toluidide

As for Example 1, 2-cyano-N-methyl-o-acetotoluidide, colorless needles, m.p. 70°–71.5° C. (prepared by the procedure described in U.S. Pat. No. 3,116,312), is heated with N,N-dimethylformamide dimethylacetal to give 2-cyano-3-(dimethylamino)-N-methyl-o-acrylotoluidide as colorless prisms, m.p. 134°–137° C.

A 0.010 mole amount of the preceding compound is refluxed in ethanol with hydrazine hydrate as for Example 1 to give the desired product as colorless prisms, m.p. 136°–136.5° C.

EXAMPLE 18

5-Amino-2'-ethyl-1,3-dimethyl-4-pyrazolecarboxanilide

As for Example 1, 2-cyano-2'-ethylacetanilide is heated with N,N-dimethylacetamide dimethylacetal to give 2-cyano-3-dimethylamino-2'-ethylcrotonanilide as colorless prisms, m.p. 79°–81.5° C.

A 0.010 mole amount of the above compound is refluxed in ethanol with hydrazine hydrate, by the procedure of Example 1 to give the product of the Example as colorless prisms, m.p. 136°–136.5° C.

EXAMPLE 19

5-Amino-2'-isopropyl-1,3-dimethyl-4-pyrazolecarboxanilide

As for Example 1, 2-cyano-2'-isopropylacetanilide, off-white crystals, m.p. 74°–78° C. (prepared by the procedure described in U.S. Pat. No. 3,116,312), is heated with N,N-dimethylacetamide dimethylacetal to yield 2-cyano-3-dimethylamino-2'-isopropylcrotonanilide as colorless prisms, m.p. 119°–121° C.

A 0.010 mole amount of the preceding compound is refluxed in ethanol with hydrazine hydrate, by the procedure of Example 1 to give the desired product as colorless crystals, m.p. 144°–146.5° C.

EXAMPLE 20

5-Amino-4'-chloro-3-ethyl-1-methyl-4-pyrazolecarboxanilide

A 20.0 g. amount of 4'-chloro-2-cyanoacetanilide, a white crystalline material, m.p. 206°–206.5° C. (prepared by the procedure described in U.S. Pat. No. 3,116,312), and 150 ml. of triethyl orthopropionate is refluxed for 6 hours. The reaction mixture volatiles are evaporated in vacuo to give a solid. The solid is recrystallized from ethanol to give trans-4'-chloro-2-cyano-3-ethoxy-2-pentenanilide as colorless prisms, m.p. 177°–178° C.

A 0.010 mole amount of the above compound is refluxed in ethanol in the presence of hydrazine hydrate as for Example 1 to give the product of the Example as pale yellow prisms, m.p. 147°–148.5° C.

EXAMPLE 21

5-Amino-3'-chloro-3-ethyl-1-methyl-4-pyrazolecarboxy-o-toluidide

A 20.0 g. amount of 3'-chloro-2-cyano-acetotoluidide, a white crystalline product, m.p. 178.5°–179.5° C. (prepared by the procedure described in U.S. Pat. No. 3,116,312), and 150 ml. of triethyl orthopropionate is refluxed for 6 hours. The reaction mixture volatiles are evaporated in vacuo to give a solid. The solid is recrystallized from ethanol to give 12.75 g., m.p. 130°–133.5° C., of a mixture of the two isomeric ethoxypropylidene derivatives.

A 0.010 mole amount of the preceding mixture is refluxed in ethanol with hydrazine hydrate as for Example 1 to give the desired product as colorless needles, m.p. 147°–149° C.

We claim:

1. The compound 5-amino-N-benzyl-1-methyl-4-pyrazolecarboxamide.
2. The compound 5-amino-N-o-chlorobenzyl-1-methyl-4-pyrazolecarboxamide.
3. The compound 5-amino-1-methyl-2'-(1-pyrrolyl)-4-pyrazolecarboxanilide.

* * * * *